United States Patent
Toh

[19]

[11] Patent Number: 6,141,040
[45] Date of Patent: Oct. 31, 2000

[54] MEASUREMENT AND INSPECTION OF LEADS ON INTEGRATED CIRCUIT PACKAGES

[75] Inventor: Peng Seng Toh, Parc Oasis, Singapore

[73] Assignee: Agilent Technologies, Inc., Palo Alto, Calif.

[21] Appl. No.: 08/995,057

[22] Filed: Dec. 19, 1997

[51] Int. Cl.[7] .............................. H04N 7/18; G06K 9/00
[52] U.S. Cl. ......................... 348/126; 348/87; 382/145; 382/147; 356/237.5
[58] Field of Search ........................... 348/87, 92, 94–95, 348/126, 133, 125; 382/141, 145, 147; 356/237, 237.4, 237.5

[56] References Cited

U.S. PATENT DOCUMENTS

| | | | |
|---|---|---|---|
| 5,162,866 | 11/1992 | Tomiya et al. | 356/237 |
| 5,249,239 | 9/1993 | Kida | 348/126 |
| 5,402,505 | 3/1995 | Roy et al. | 348/126 |
| 5,406,372 | 4/1995 | Vodanovic et al. | 348/87 |
| 5,414,458 | 5/1995 | Harris et al. | 348/92 |
| 5,528,371 | 6/1996 | Sato et al. | 348/126 |
| 5,550,583 | 8/1996 | Amir et al. | 348/126 |
| 5,909,285 | 6/1999 | Beaty et al. | 348/126 |
| 5,910,844 | 6/1999 | Phillips et al. | 348/126 |
| 5,926,278 | 7/1999 | Asai | 348/126 |
| 5,995,216 | 11/1999 | Moriya et al. | 356/237 |
| 5,995,220 | 11/1999 | Suzuki | 356/237.5 |
| 6,064,756 | 5/2000 | Beaty et al. | 348/87 |

FOREIGN PATENT DOCUMENTS

| | | | |
|---|---|---|---|
| 9100023 | 3/1991 | Belgium | H05K 13/08 |

*Primary Examiner*—Vu Le

[57] ABSTRACT

A system of optics, cameras and image processor arrangement capable of capturing images of lead tips of object fields resulting in accurate 3 dimensional positions of all the leads on a Integrated Circuit such as a Quad Flat Package (QFP). The system comprises of a telecentric lens attached to a camera working with an arrangement of mirrors and lighting. The telecentric lens and mirror optical layout splits the acquired image into 2 orthogonal viewing fields of the same lead tips of the QFP. The QFP is placed flat on a pedestal, and for any given side of the QFP, the first field views the lead tips from the front. The second field views the lead tips from the bottom of the IC package. Enhanced lead tip images are acquired by a lighting arrangement that casts illumination on the lead tips only. Electronic processing techniques are used to compute the geometry of the laeds such as global coplanarity, lead standoff and inspection of other lead defects.

6 Claims, 7 Drawing Sheets

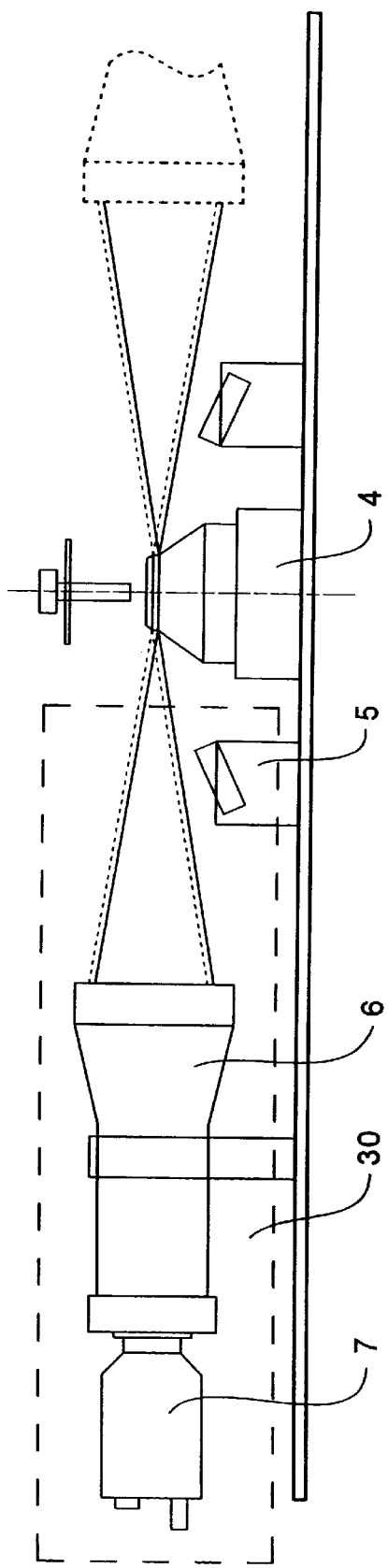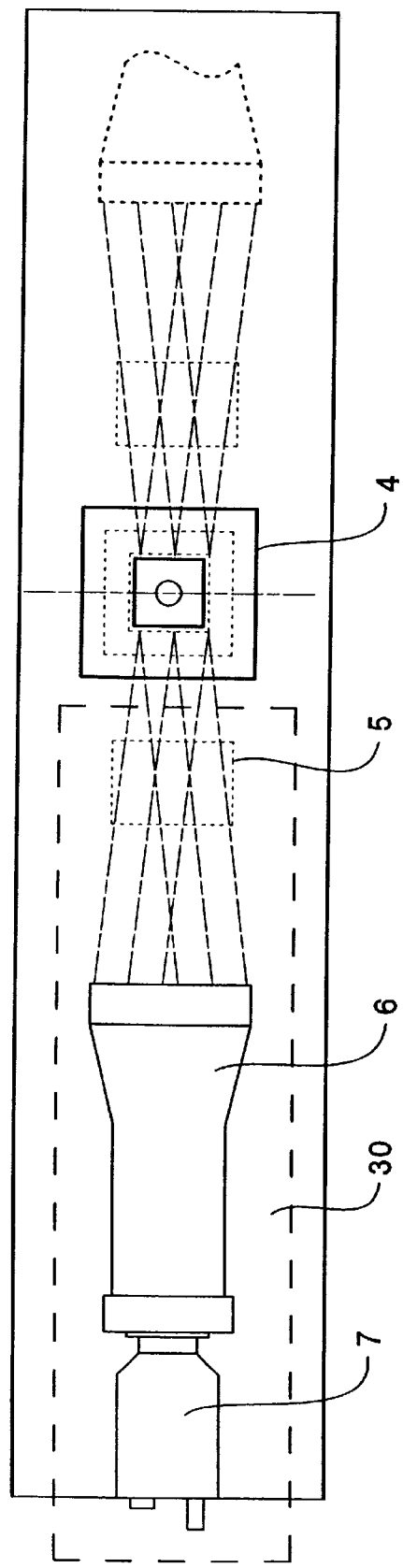
Fig. 3a
Fig. 3b

MEASUREMENT AND INSPECTION OF LEADS ON INTEGRATED CIRCUIT PACKAGES

FIELD OF INVENTION

The present invention relates to a method and apparatus for inspection of leads on an integrated circuit package.

DESCRIPTION OF PRIOR ART

An Integrated Circuit (IC) package commonly has a square or rectangular plastics package moulded over the IC circuitry commonly known as the "die". The size of the package may range from 4×4 mm square to 32×32 mm square. Extending from the plastics package are leads which provide electrical connectivity point from the die inside the IC package to the printed circuit boards (PCB). It is often important for the IC package and the leads to possess accurate and consistent mechanical dimensions due to the use of highly automated PCB assembly machine to place and solder the ICs onto the PCB. In particular, for high lead count IC such as the Quad Flat Pack (QFP) which has leads on all four sides of the package, the mechanical requirements are even more stringent. There are several requirements of the leads and defect categories that have to be measured include coplanarity, lead pitch, terminal dimension, standoff and others. Lead defects include bent leads, solder plating defects, swept leads, burr and others.

Several techniques and systems consist of special optical and lighting arrangements for the direct and indirect viewing of leads of IC packages are available on the market. There are two major categories of IC lead inspection and measurement systems. One category uses laser scanning approach. The other commonly used techniques include shadow casting and back illuminating the lead profiles onto imaging planes. Examples of some prior art IC lead inspection techniques are mentioned below.

U.S. Pat. No. 5,406,372 assigned to Modular Vision Systems Inc. describes a method of using a pair of lasers to scan the leads from the top without contact.

U.S. Pat. Nos. 5,414,458 assigned to Texas Instruments Incorporated describes a back illuminated system with image doubler that increased the resolution of the image.

U.S. Pat. No. 5,402,505 also assigned to Texas Instruments Incorporated describes a lead inspection system to locate the leads with reference to a reference plate on which the device is mounted, and a real-time reference which is used to provide a known correlation between the image pixels and linear measurement.

U.S. Pat. No. 5,162,866 assigned to Sony Corporation describes a method for inspecting IC leads comprising at least a displacement sensor in which the upward and downward coplanarity error of each lead is measured from a level change in the output signal of the sensor.

PCT/BE91/00023 assigned to ICOS Vision System NV of Belgium describes a method and device for determining a position of at least one lead of an electronic component using shadow casting techniques.

Most of these techniques do not view the lead directly with front lighting. The operation of direct lead front viewing methods are mostly back illuminated and views of the leads are from a single front direction with the QFP rotated so the images of leads on all 4 sides can be captured. Back illumination cannot reveal the surface property of a lead and does not produce a gray scale image. Back illumination is suitable for producing a binary instead of a gray scale image. Image processing applied to binary image is limited in its capability as it does not contain as much information as the gray scale image. Sub-pixel edge detection which is crucial to high precision measurement cannot be effectively applied to binary images. The shadow casting method measures the geometry of the top surface of a lead. The variation in foot angle of a lead will also affect the accuracy obtainable from the shadow casting approach.

In the case of laser scanning technique, the top surface instead of the bottom surface of a lead is measured. In actual requirement, the bottom surface and geometry of a lead is more importance than the top surface because of the electrical connectivity. The thickness of a lead will vary from lead to lead and so is the solder plating thickness. Hence measuring the top surface is not equivalent to measuring the bottom surface. This is especially true in high precision measurement in the range of several micrometer. The laser scanning technique cannot detect burr on lead tips which is another important factor in electrical connectivity. Burr on lead tips is common due to the trim and form process.

SUMMARY OF THE INVENTION

In accordance one aspect of the present invention, a method for inspection of leads of an integrated circuit package is provided. An embodiment of the method includes obtaining first and second images of respective substantially orthogonal views of a plurality of leads along a side of an integrated circuit package, the first and second images preferably both being substantially front lit.

In a second aspect, the invention also provides an apparatus for inspecting leads of an integrated circuit package. An embodiment of the apparatus comprises an imager arranged to obtain first and second images of respective orthogonal views of leads on an integrated circuit package, and lights arranged so as to provide substantially front light for each of the first and second images.

Preferably a reflector such as an angled mirror is employed in order to orthogonally project an underside view of the leads, such that a side or front view and the projected orthogonal underside view can be obtained simultaneously.

In a preferred form of the invention, a telecentric lens is used having a high F-number with a long working distance that compensates for the different object distances of the two orthogonal views. A camera, such as a digital video or still cameras, is preferably coupled to the telecentric lens in order to store the acquired images for processing.

In the preferred form of the invention, the first and second images are processed using edge detection techniques to determine relative positional characteristics of the leads.

Further features and advantages of the invention can be understood from the following description of a preferred form thereof, as well as from the appended claims.

BRIEF DESCRIPTION OF THE DRAWINGS

The invention is described in greater detail hereinbelow, by way of example only, with reference to the accompanying drawings, wherein:

FIG. 3A and FIG. 3B (showing the side view and bottom view, respectively) are an overall optical arrangement of an embodiment of the invention;

DETAILED DESCRIPTION OF SPECIFIC EMBODIMENT OF THE INVENTION

Figure 1A:
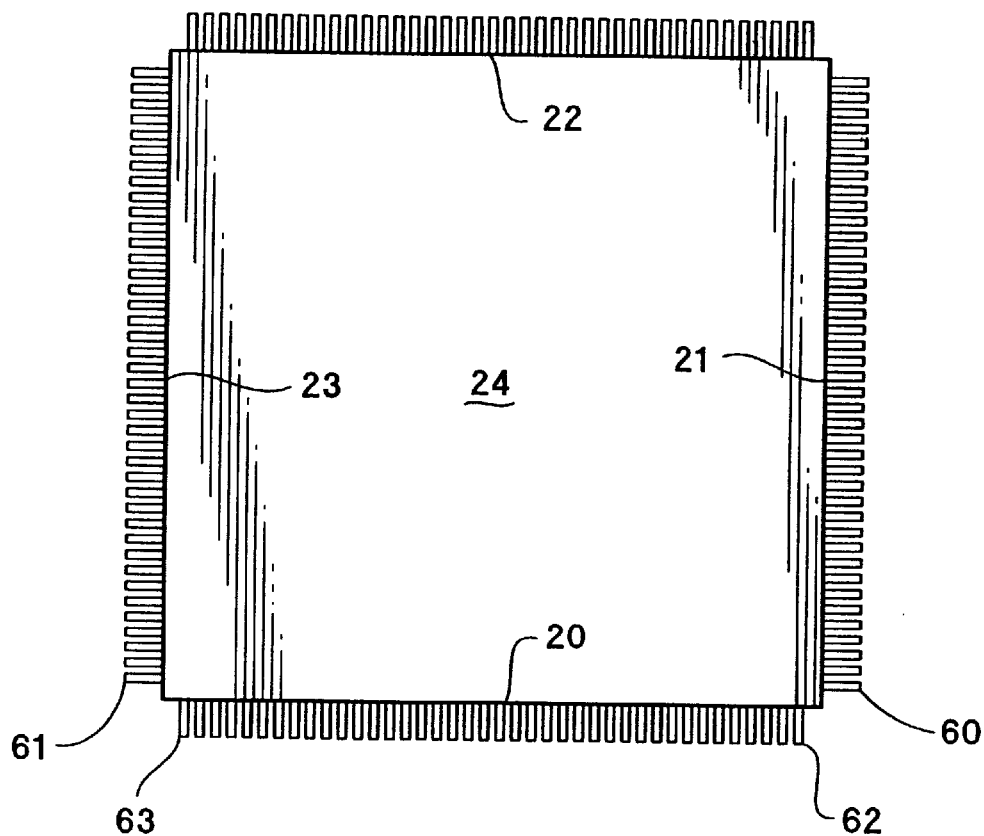
FIG. 1*a* is a plan view of a typical QFP IC.

An embodiment of the present invention is described hereinbelow. This embodiment operates to capture two views of a plurality of leads on an integrated circuit and these two views are made orthogonal by systematic arrangement of optics and mirrors. The image acquisition optics includes a telecentric optical system and a reflecting mirror arranged for the relay and folding of viewing fields for generating simultaneous aligned orthogonal views of the leads along a side of an IC. From the orthogonal properties of the images, the three dimensional position of each lead can be accurately computed and major lead defects can be inspected. In a preferred embodiment, the frontal object field of the leads constitutes one view and the bottom side of the same leads constitutes the other view. The view that captures the frontal image of the plurality of leads is hereinafter known as the front, side or edge view, and the view that captures the bottom side of the plurality of leads is hereinafter known as the bottom or underside view. The frontal and bottom views of the plurality of leads are simultaneously imaged onto the same video camera and appear on the image hereinafter known as the orthogonal lead image. The orthogonal lead image includes of the front view aligned on top of the bottom view.

Using the Cartesian coordinate system, the front view of the plurality of leads is defined by the X-Z plane; while the bottom view is defined by the X-Y plane. The Z axis is related to the height of the leads and hence can be used to compute the coplanarity measurement; the X axis is related to the inter-spacing between leads and hence the lead pitch measurement; the Y axis is related to the extension of the leads and hence measures the terminal dimension of the IC.

Front lighting is used which illuminates the front and bottom surfaces of the plurality of leads. The viewing geometry of the video camera and the illumination angle provides a significant contrast on the lead tips. The bottom edge of a lead tip represents the real contact area of the lead with another surface. In the case of placing the IC onto a PCB, the real contact of an IC with the PCB is the bottom surface of the lead tip. Unlike back lighting or shadow casting, the use of front lighting allows gray scale images to be captured. Sub-pixel accuracy edge detection and surface defects can be detected from gray scale images rather than binary images. Simultaneous acquisition of all four sided images of an integrated circuit is possible with the use of front lighting. In the case of back lighting, simultaneous acquisition of all four sided images of an integrated circuit such as a QFP is not possible.

Following image acquisition, the orthogonal lead image, which includes the front view and the bottom view, is subject to image analysis to determine the coordinate of the tip of each lead. In the image analysis, edge detection algorithms are applied in both the horizontal and vertical directions to both the top view and bottom view. An orthogonal lead image contains the entire row of leads distributed along a single side of a QFP as well as the two extreme leads of the adjacent sides. The two extreme leads that appear in an orthogonal lead image is hereinafter known as the corner leads. The coordinate of one side of a QFP is related to the adjacent side by the coordinate of the corner leads. The embodiment of the invention described hereinbelow allows the flexibility of using one set of optical system combined with the rotation of the QFP for the acquisition of orthogonal leads images of all the four sides of a QFP; or using multiple sets of optical system to acquire the orthogonal lead images of different sides of leads of a QFP simultaneously.

Figure 1B:
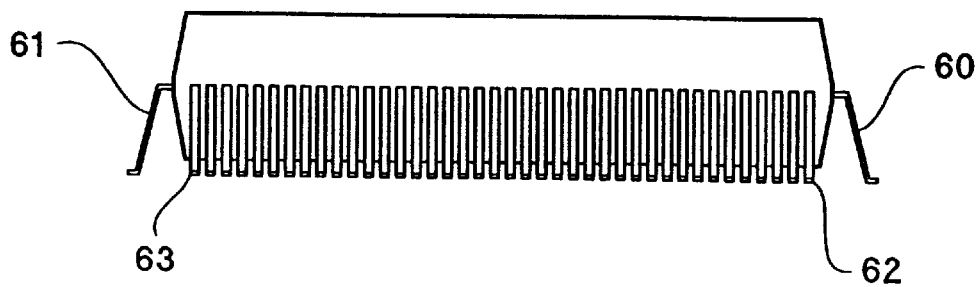
FIG. 1*b* is a front view of a typical QFP IC.
Figure 2:
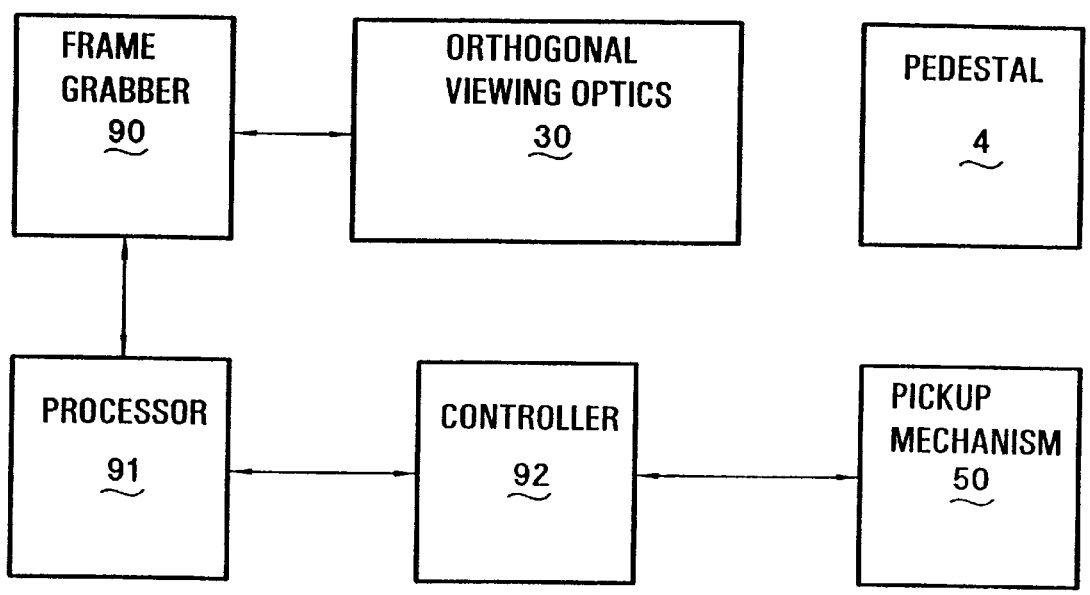
FIG. 2 is a system block diagram of an embodiment of the invention.
Figure 4:
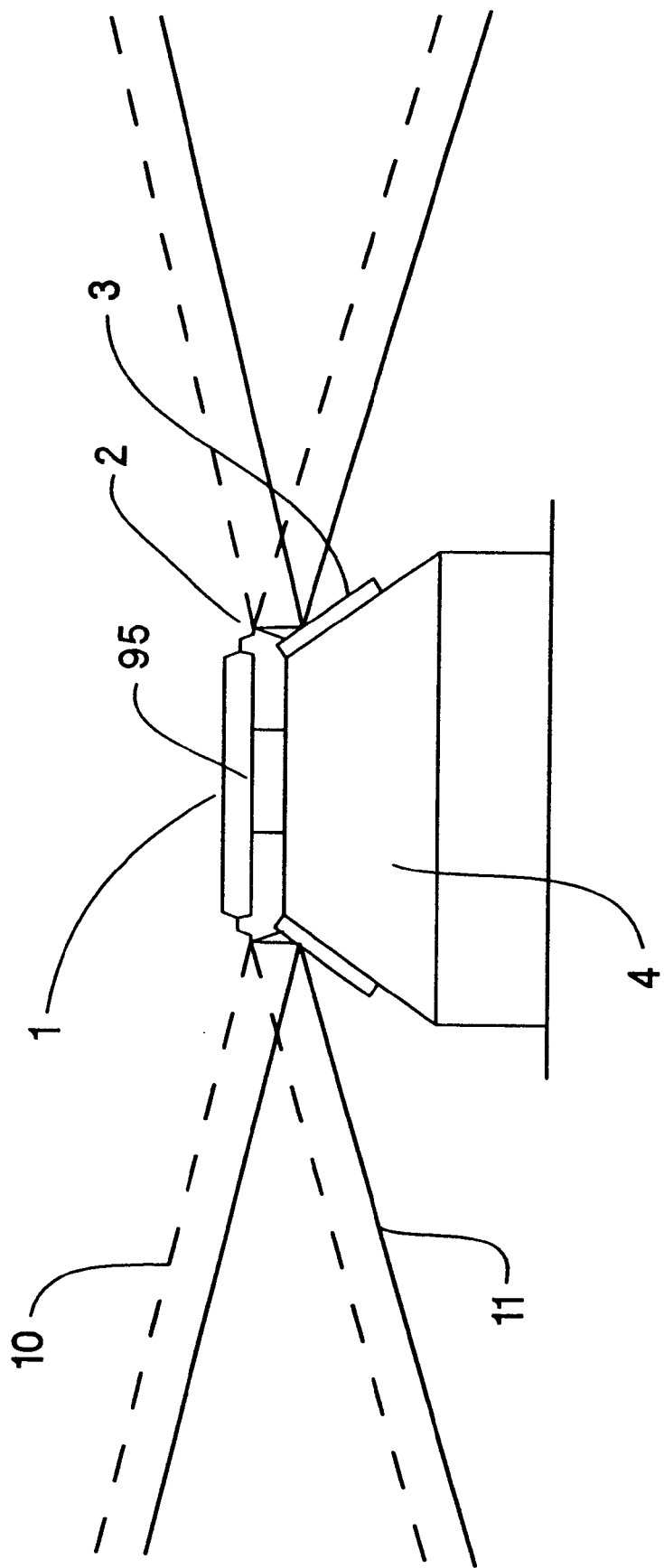
FIG. 4 is a side view of a pedestal design.

According to an embodiment of the invention, an optical and imaging system for simultaneously capturing two orthogonal views of a plurality of leads on a side of an integrated circuit is shown in FIG. 3. A side view FIG. 3A) and plan view (FIG. 3B) of an optical arrangement of an imaging system is illustrated in respective upper and lower drawings in FIGS. 3A and 3B. A close-up side view of a pedestal for the imaging system is shown in FIG. 4. An example of a QFP is shown in plan and edge views in FIGS. 1a and 1b respectively. A QFP mounted on a pedestal 4 is shown in FIG. 4. A block diagram of an imaging system is shown in FIG. 2.

As illustrated in FIG. 3 and FIG. 4, the embodiment of the imaging system comprises a telecentric lens 6, underside reflecting mirror 3, video camera 7, and front illuminating light source 5, which is inclined at an angle with respect to the plurality of leads 2. The telecentric lens 6 relays the two orthogonal views onto a common video camera 7. One view is obtained from a direct side (e.g. viewed from the edge of the IC e.g., QFP) of the leads on the IC, and an orthogonal view is obtained from an underside image of the leads reflected in the underside reflecting mirror 3. A QFP mounted on pedestal 4 is viewed by viewing optics 30. The video camera 7 is further connected to a frame grabber 90 and processor 91 (FIG. 2), which digitizes and analyses the image respectively. The optical system, which contains the telecentric lens 6, the underside reflecting mirror 3, the video camera 7, and the front illuminating light source 5, is hereinafter collectively called the orthogonal viewing optics 30.

Figure 5:
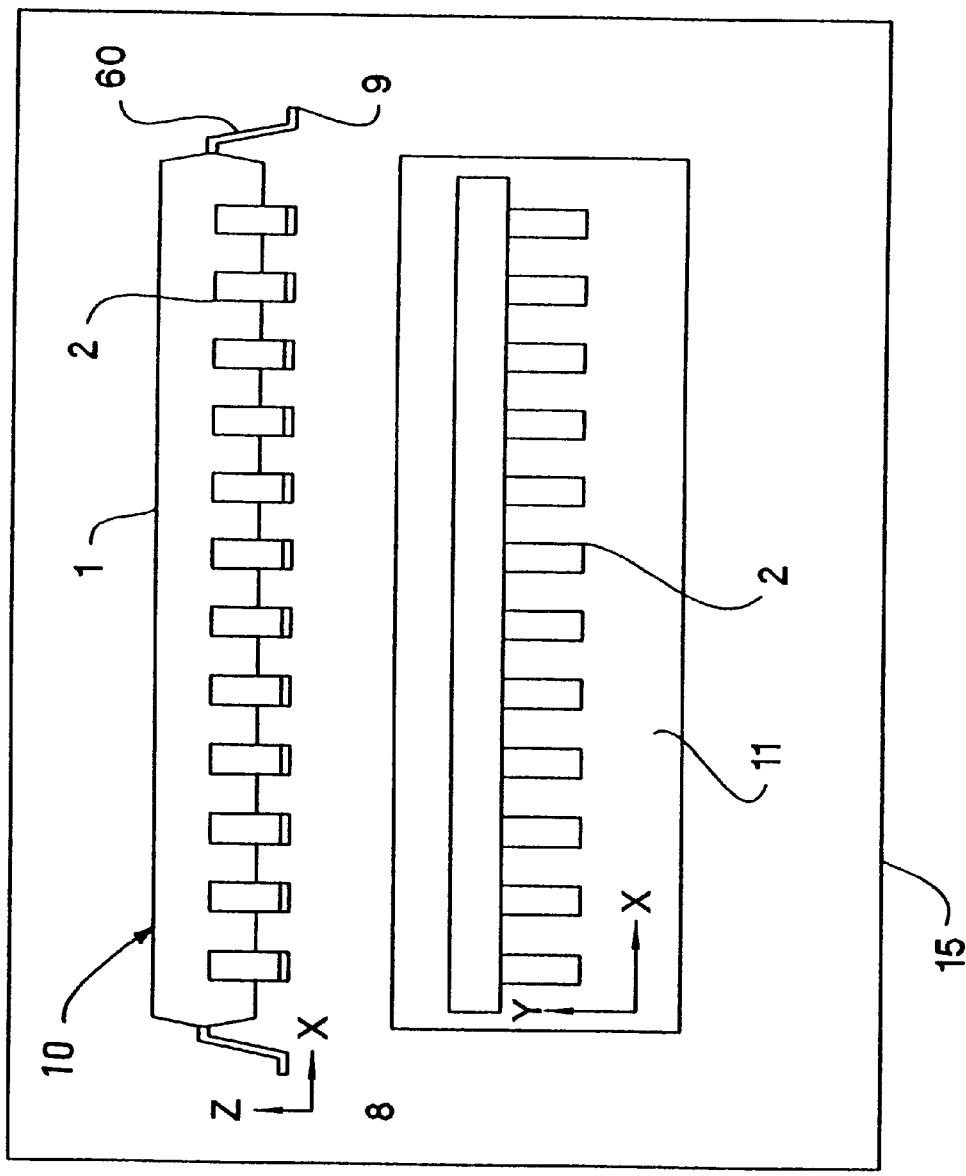
FIG. 5 illustrates an image consisting of orthogonal views of a plurality of leads on a row.

An example of an orthogonal lead image 15 obtained from the orthogonal viewing optics 30 is illustrated in FIG. 5. FIG. 5 shows a front view 10 and simultaneously obtained underside view 11 of the IC leads 2. The lens of the orthogonal viewing optics 30 includes a high F-number telecentric lens 6 with a long working distance. The telecentricity is designed to be less than 0.1 degree to reduce computational errors. The front of the object field of the telecentric lens 6 is directed at the lead tips 8 of the leads 2 to acquire a front view of the plurality of leads 2. The telecentric nature of the telecentric lens 6 will result in an image that contains the front view 10 aligned on top of the bottom view 11. The telecentricity of the telecentric lens compensates for the different object distance of the front view and bottom view.

As shown in FIGS. 3 and 4, the bottom region of the object field of the telecentric lens 6 is reflected off the underside reflecting mirror 3 positioned beneath the leads 2 of the QFP 1. The underside reflecting mirror 3 is mounted on a pedestal 4 where the QFP 1 is placed during inspection. The underside reflecting mirror 3 is usually mounted at about 45 degree with respect to the datum 95 of the pedestal 4. The datum 95 of the pedestal 4 is the top surface plane where the QFP 1 is placed during inspection. The bottom side of the plurality of leads 2 will be reflected off the underside reflecting mirror 3 into the telecentric lens 6 to produce the bottom view 11. Due to the telecentricity of the telecentric lens 6, both views will appear focused on the video camera 7.

During operation, a QFP 1 is picked up by a pickup mechanism 50 and placed onto the pedestal 4 for measurement and inspection. The motion of the pickup mechanism 50 is controlled by a programmable logic controller 92 which in turn receives instructions from the processor 91. The function of the pickup mechanism 50 is to pickup the QFP package body 24 and place it centrally and flatly onto the pedestal datum 95.

In the preferred embodiment, an array of LEDs is used as the light source 5 see FIGS. 3A and 3B. The width of the light source 5 is greater than the side length of the IC carrying plurality of leads 2 being inspected. A diffuser is attached to the LED array to provide uniform illumination. The light source 5 is inclined at an angle with respect to the plurality of leads 2 such that the lead tips 8 and the bottom side of the plurality of leads 2 are clearly illuminated. The light source 5 is positioned below the telecentric lens 6 such that it will not obstruct the imaging path of the said telecentric lens 6. A significant contrast is created between the background and the plurality of leads 2 due to the light source 5 illumination arrangement.

Figure 7A:
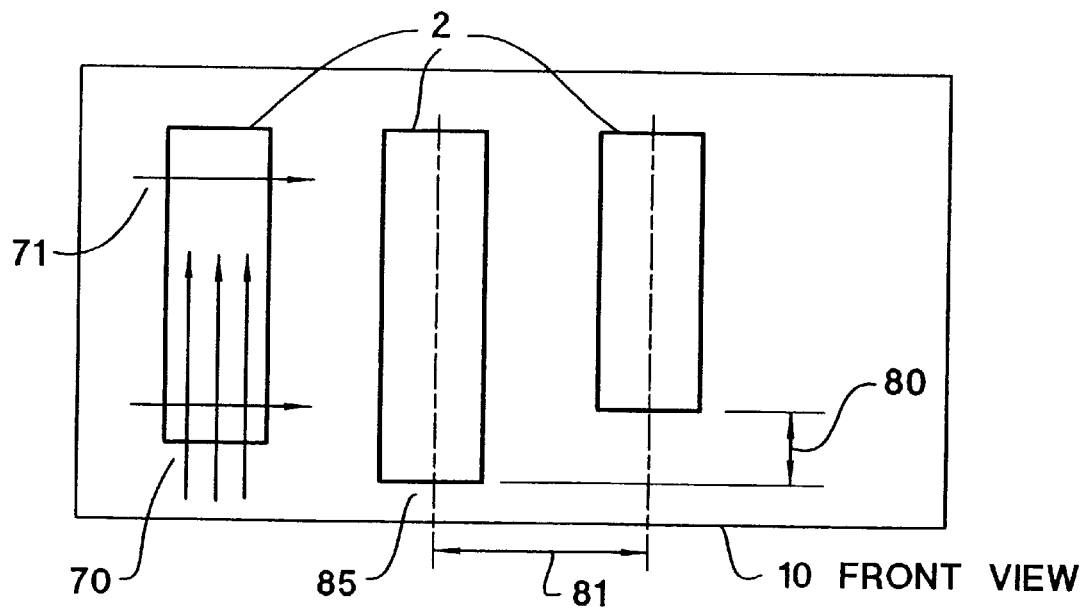
FIG. 7 illustrates the computation of IC lead global coordinates showing front view and bottom view.
Figure 7B:
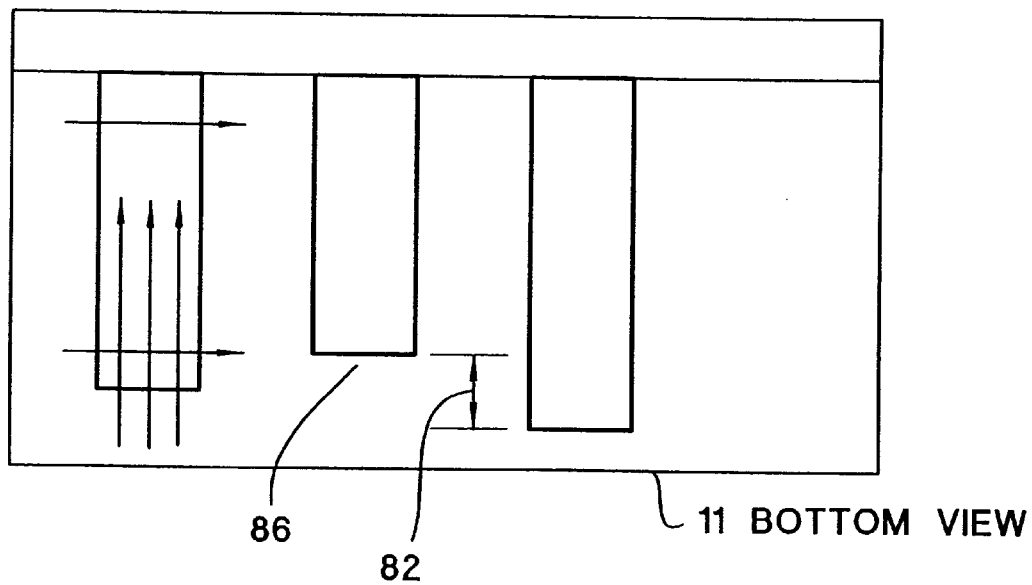

The orthogonal lead image 15 is subject to image analysis by the processor 91 to determine the coordinate of the tip 8 of each of the plurality of leads 2. The image analysis means contains edge detection algorithms performed by the processor on the orthogonal lead image 15 applied in both the horizontal 71 and vertical directions 70 (FIG. 7) to the front view 10 and the bottom view 11. The edge detection algorithms detect the edges 85 of the leads surrounding the lead tip area. In most cases, an orthogonal lead image 15 contains the entire row of leads distributed on a single side of a QFP 1 as well as the two extreme leads 60, 61 of the adjacent sides (see FIGS. 1a, 1b and FIG. 5). The two extreme leads that appear in the orthogonal lead image are hereinafter known as the corner leads 60 and 61. Edge detection is similarly applied to detect the tip 9 of the corner leads 60 and 61. The coordinate of one side of an QFP 1 is related to the adjacent side by the coordinates of the corner leads 60 and 61.

The illustrated embodiment of the present invention allows the flexibility of using one set of orthogonal viewing optics 30 combined with the rotation of the QFP 1 for the acquisition of orthogonal lead images 15 for all the four sides 20, 21, 22 and 23 of the QFP 1. An alternative is to use multiple sets of orthogonal viewing optics 30 to acquire the orthogonal lead images 15 of different sides 20, 21, 22 and 23 of leads 2 on the QFP 1 simultaneously. The rotation of the QFP 1 can be effected by the pickup mechanism 50. FIGS. 3A and 3B illustrates an example of using two sets of orthogonal viewing optics which view the QFP 1 from two directly opposite sides. In order to complete the viewing of all four sides, the QFP 1 has to be rotated by the pickup mechanism 50. Alternatively, four sets of orthogonal viewing optics 30 could similarly be used to view all the four sides of a QFP 1 simultaneously. Using four sets of such orthogonal viewing optics requires no rotation of the QFP 1, thus reduces the overall measurement time.

In the case where only one set of orthogonal viewing optics 30 is being used, the pickup mechanism 50 is required to rotate the QFP 1 four times sequentially. For example, the orthogonal viewing optics 30 first views side 20 of the QFP 1, the pickup mechanism 50 then rotates the QFP by 90 degree sequentially so that sides 21, 22 and 23 will be acquired and analysed eventually. Following from this particular system arrangement and the QFP motion sequence, the Z coordinate of a row of leads on one side of the QFP can be related to the adjacent side by the corner leads. The Z coordinate of a corner lead 60 in one orthogonal lead image 15 is the same as the first lead 63 after the QFP has been rotated by 90 degree. Hence the Z coordinate of an orthogonal lead image 15 is related to its adjacent orthogonal lead image 15 by the corner lead 60 and the first lead 63. Similarly, corner lead 61 is related to the last lead 62.

The location of the lead tips 8 of the QFP 1 is computed by the processing unit 91 through the use of a sub-pixel edge detection algorithm. For those skilled in the art of image processing, edge detection techniques such as Difference of Gaussian (DOG), Laplacian of Gaussian (LOG), Canny operator and others are known and can be applied to locate the lead tips positions. The lead tips 8 of the bottom view 11 can be similarly detected by the said edge detection method. In order to obtain the global coordinate of each of the lead tips, the said edge detection algorithms must be applied in both the horizontal 71 and vertical 70 direction for each of the two orthogonal views 10 and 11.

In the front view 10, the horizontal edge detector 71 will locate the X coordinates of the plurality of leads 2. A single lead has two edges which correspond to the left edge $X_1$ and the right edge $X_2$ respectively. The horizontal coordinate of the centre $X_c$ of the two lead edges is defined by $X_c=(X_1+X_2)/2$. The vertical coordinate of the lead tips 8 of the front view 10 corresponds to the Z axis. The vertical direction edge detection algorithm 70 will locate several edge locations of a lead tip due to its width. An average value of the edge locations is computed. This coverage value corresponds to the Z position of the lead tip 8. With the application of both horizontal and vertical edge detection algorithm, the centre lead tip coordinate 85 is computed (Xc, Zc). The algorithms are applied to each of the plurality of leads 2 within the orthogonal lead image 15. Hence, the pitch 81 and height difference 80 between adjacent leads can be found as follows:

$$\text{pitch }(n)=abs\ \{Xc(n)-Xc(n+1)\}$$

$$\text{height }(n)=abs\ \{Zc(n)-Zc(n+1)\}$$

where n is the $n^{th}$ lead.

For the lead tips 8 of the bottom view 11, the similar set of edge detection algorithms will result in the detection of lead tip coordinate 86 defined by (Xc, Yc). Hence the global coordinate of any lead tips can be found by applying the lead tips detection algorithms to both the front 10 and bottom views 11. The global coordinate of a lead is hence defined by (Xc, Yc, Zc).

Figure 6:
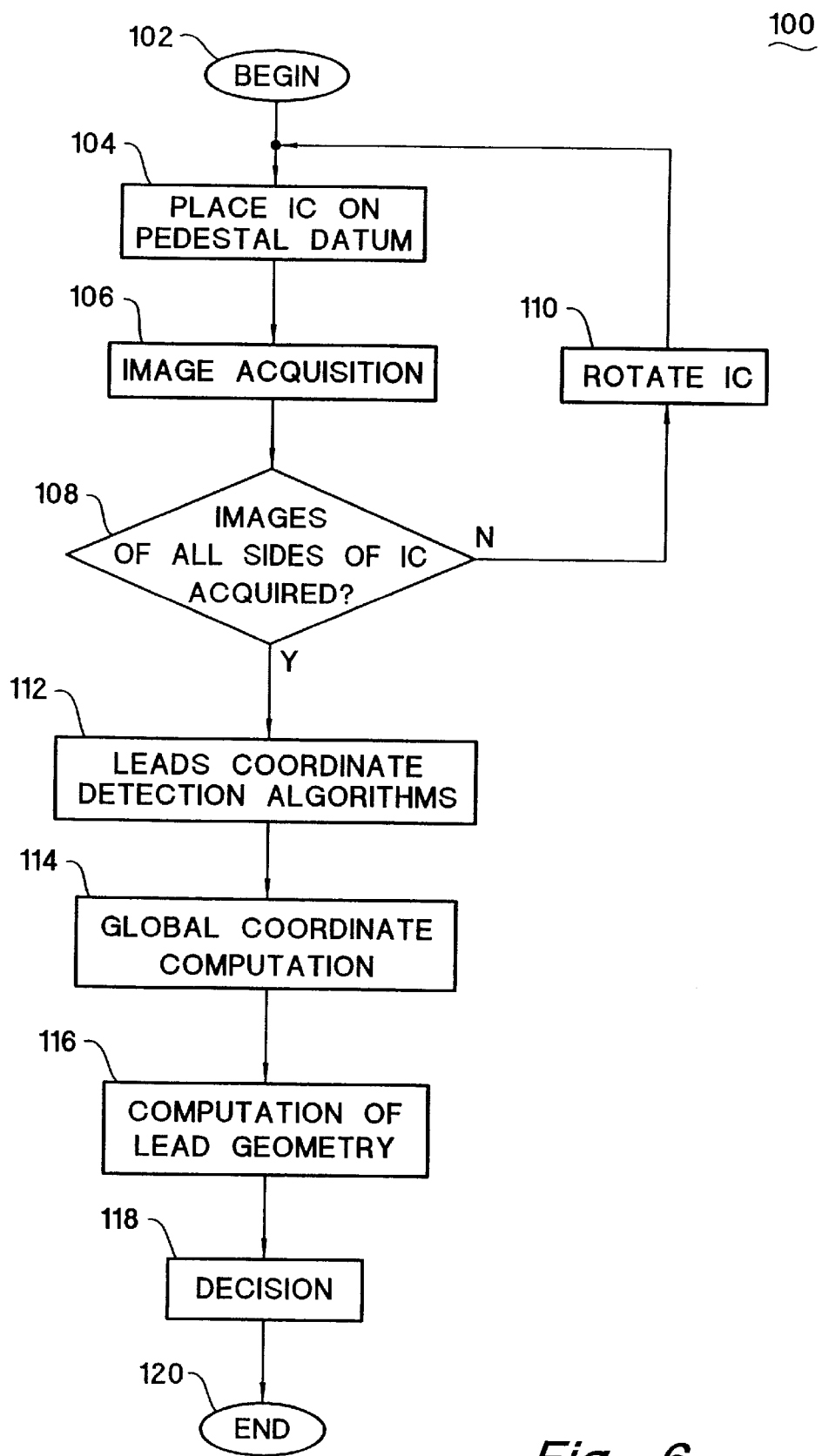
FIG. 6 is a flow chart of image analysis algorithm.

A flowchart 100 illustrating the operations described hereinabove is shown in FIG. 6, beginning with step 102. As shown, an orthogonal lead image 15 for the leads on each side of the IC is obtained during steps 104, 106, 108, 110, with the rotation of the IC (step 110) and iteration of the image acquisition step if required. The positional attributes of the leads are then determined at steps 112, 114, and 116 through computations performed on the lead images, such that at step 118 one can decide whether the leads meet predetermined requirements. For example, the lead geometry obtained at step 116 may be compared with prestored tolerances to facilitate the decision step 118. Following the decision the procedure ends at step 120.

The foregoing detailed description of the present invention has been presented by way of example only, and is not intended to be considered limiting to the invention as defined in the appended claims.

What is claimed is:

1. An apparatus for inspecting leads of an integrated circuit package, comprising:
   a pedestal having a top surface plane for receiving an integrated circuit package with leads extending from one side,
   an angled reflector positioned on the pedestal adjacent the top surface plane and beneath the leads of the integrated circuit package to reflect a bottom view of the leads, and
   an imaging system arranged on said one side of the integrated circuit package to acquire an image, the image comprising a direct side view of the leads, and the bottom view of the leads reflected by the reflector, the side and bottoms views being substantially orthogonal.

2. An apparatus as claimed in claim 1, further comprising a light source arranged on said one side of the integrated circuit for front-illuminating the leads.

3. An apparatus as claimed in claim 1, further comprising a processor for processing the image of the side and bottom views of the leads to determine the relative positions of the leads.

4. An apparatus as claimed in claim 3, wherein the processor includes an edge detection algorithm to detect the edges of the leads from the image of the side and bottom views.

5. An apparatus as claimed in claim 1, wherein the imaging system comprises a telecentric lens and a camera, the lens receiving a direct side view of the leads and the bottom view of the leads reflected by the reflector, and relaying the side and bottom views to the camera.

6. A method of inspecting leads of an integrated circuit package, comprising:
   providing a pedestal having a top surface plane,
   positioning on the top surface plane of the pedestal an integrated circuit package with leads extending from one side,
   providing an angled reflector adjacent the top surface plane of the pedestal and beneath the leads of the integrated circuit package to reflect a bottom view of the leads, and
   providing an imaging system on said one side of the integrated circuit package to acquire an image, the image comprising a direct side view of the leads, and the bottom view of the leads reflected by the reflector, the side and bottoms views being substantially orthogonal.

* * * * *